US008124564B2

(12) United States Patent
Röchling et al.

(10) Patent No.: US 8,124,564 B2
(45) Date of Patent: Feb. 28, 2012

(54) USE OF ALKYL CARBOXYLIC ACID AMIDES AS PENETRATION ENHANCERS

(75) Inventors: Andreas Röchling, Langenfeld (DE); Karl Reizlein, Monheim (DE); Peter Baur, Schondorf (DE)

(73) Assignee: Bayer CropScience AG, Monheim (DE)

( * ) Notice: Subject to any disclaimer, the term of this patent is extended or adjusted under 35 U.S.C. 154(b) by 86 days.

(21) Appl. No.: 11/568,370

(22) PCT Filed: Apr. 22, 2005

(86) PCT No.: PCT/EP2005/004342
§ 371 (c)(1),
(2), (4) Date: Apr. 26, 2007

(87) PCT Pub. No.: WO2005/104844
PCT Pub. Date: Nov. 10, 2005

(65) Prior Publication Data
US 2007/0293550 A1    Dec. 20, 2007

(30) Foreign Application Priority Data

Apr. 27, 2004   (DE) .................... 10 2004 020 840

(51) Int. Cl.
A01N 25/26      (2006.01)
A01N 37/18      (2006.01)
A01N 25/30      (2006.01)
A01N 47/36      (2006.01)
A01N 43/653     (2006.01)
A01N 43/56      (2006.01)
A01N 43/30      (2006.01)

(52) U.S. Cl. ........................................ 504/100
(58) Field of Classification Search .................. None
See application file for complete search history.

(56) References Cited

U.S. PATENT DOCUMENTS

| | | | |
|---|---|---|---|
| 5,206,225 A | | 4/1993 | Horstmann et al. |
| 5,230,892 A | | 7/1993 | Feyen et al. |
| 5,354,726 A | | 10/1994 | Narayanan et al. |
| 5,489,569 A | * | 2/1996 | Bryant et al. ............ 504/166 |
| 5,599,828 A | | 2/1997 | Zeun et al. |
| 5,741,502 A | | 4/1998 | Roberts |
| 5,789,430 A | | 8/1998 | Jautelat et al. |
| 5,859,039 A | * | 1/1999 | Jautelat et al. ............ 514/384 |
| 5,998,455 A | | 12/1999 | Knauf-Beiter et al. |
| 6,306,850 B1 | | 10/2001 | Dutzmann et al. |
| 6,355,634 B1 | | 3/2002 | Isenring et al. |
| 6,407,100 B1 | | 6/2002 | Isenring et al. |
| 6,602,823 B1 | | 8/2003 | Röchling et al. |
| 7,329,618 B2 | | 2/2008 | Dunkel et al. |
| 7,521,397 B2 | | 4/2009 | Dunkel et al. |
| 7,754,655 B2 | | 7/2010 | Wolf et al. |
| 7,799,737 B2 | | 9/2010 | Rosenfeldt et al. |
| 2002/0173529 A1 | | 11/2002 | Dutzmann et al. |
| 2004/0157743 A1 | | 8/2004 | Rosenfeldt et al. |
| 2005/0101639 A1 | | 5/2005 | Ammermann et al. |
| 2005/0165076 A1 | | 7/2005 | Ammermann et al. |
| 2005/0221991 A1 | | 10/2005 | Wolf et al. |
| 2006/0004070 A1 | | 1/2006 | Wachendorff-Neumann et al. |
| 2006/0014738 A1 | | 1/2006 | Wachendorff-Neumann et al. |
| 2006/0035942 A1 | | 2/2006 | Wachendorff-Neumann et al. |
| 2007/0037799 A1 | | 2/2007 | Dahmen et al. |
| 2007/0054804 A1 | | 3/2007 | Suty-Heinze et al. |
| 2007/0060579 A1 | | 3/2007 | Wachendorff-Neumann et al. |
| 2007/0298966 A1 | | 12/2007 | Fischer et al. |
| 2008/0249193 A1 | | 10/2008 | Frisch et al. |
| 2008/0269051 A1 | | 10/2008 | Suty-Heinze et al. |
| 2008/0269263 A1 | | 10/2008 | Dahmen et al. |
| 2008/0312290 A1 | | 12/2008 | Vermeer et al. |
| 2009/0018015 A1 | | 1/2009 | Wachendorff-Neumann et al. |
| 2009/0069178 A1 | | 3/2009 | Suty-Heinze et al. |
| 2009/0170918 A1 | | 7/2009 | Wolf |
| 2009/0286681 A1 | | 11/2009 | Dahmen et al. |
| 2009/0306109 A1 | | 12/2009 | Dutzmann et al. |

FOREIGN PATENT DOCUMENTS

| | | |
|---|---|---|
| EP | 0 453 899 A1 | 10/1991 |
| EP | 0 757 891 A2 | 2/1997 |
| GB | 2 262 037 A | 6/1993 |
| WO | WO 88/02216 A1 | 4/1988 |
| WO | WO 91/15119 A1 | 10/1991 |
| WO | WO 94/13140 A1 | 6/1994 |
| WO | WO 96/16048 A1 | 5/1996 |
| WO | WO 96/37494 A1 | 11/1996 |
| WO | WO 98/25923 A1 | 6/1998 |
| WO | WO 02/098230 A2 | 12/2002 |
| WO | WO 03/070705 A1 | 8/2003 |
| WO | WO 03/099005 A1 | 12/2003 |
| WO | WO 03/101197 A1 | 12/2003 |

OTHER PUBLICATIONS

Jautelat et al., JAU 6476—a new dimension DMI fungicide, The BCPC Conference: Pests and diseases, vols. 1 and 2. Proceedings of an international conference held at the Brighton Hilton Metropole Hotel, Brighton, UK, Nov. 18-21, 2002, Abstract.*
McMullen et al., Wheat Uniform Fungicide Trials, Proceedings of the National Fusarium Head Blight Forum, 2003.*
Waxman, Agrochemical and Pesticide Safety Handbook, 1998.*
Mesterházy et al., 2004, Prothioconazole fungicides against FHB in Wheat, 2003/2004 Results, in Proceedings of the 2nd International Symposium on Fusarium Head Blight Dec. 11-15, 2004, Orlando FL, Michigan State University Publishing, East Lansing, MI, pp. 355-356.*
Table of Vegetable Oil Compositions, thepaleodiet.com/nutritional_tools/oils_table.html, Mar. 17, 2011.*
Irwin, W.J., et al., "Percutaneous absorption of ibuprofen and naproxen: Effect of amide enhancers on transport through rat skin," Int. J. Pharm. 66:243-252, Elsevier Science Publishers B.V. (1990).
International Search Report for International Application No. PCT/EP2005/004342, European Patent Office, Netherlands, mailed on Oct. 10, 2005.

(Continued)

Primary Examiner — Johann Richter
Assistant Examiner — Thor Nielsen
(74) Attorney, Agent, or Firm — Sterne, Kessler, Goldstein & Fox P.L.L.C.

(57) ABSTRACT

Use of carboxamides of the formula (I)

$$R^1-CO-NR^2R^3 \quad (I),$$

in which
$R^1$ represents $C_3$-$C_{19}$-alkyl,
$R^2$ represents $C_1$-$C_6$-alkyl and
$R^3$ represents H or $C_1$-$C_6$-alkyl
for promoting the penetration of agrochemical active substances into plants.

18 Claims, No Drawings

OTHER PUBLICATIONS

Copending U.S. Appl. No. 12/677,860, inventors Häuser-Hahn, et al., 371(c) Date of Oct. 26, 2010, United States Patent Office, Alexandria, VA (United States) (Not Published).

Copending U.S. Appl. No. 12/822,261, inventors Davies, et al., filed Jun. 24, 2010, United States Patent Office, Alexandria, VA (United States) (Not Published).

Copending U.S. Appl. No. 12/836,727, inventors Andersch, et al., filed Jul. 15, 2010, United States Patent Office, Alexandria, VA (United States) (Not Published).

Copending U.S. Appl. No. 12/881,281, inventors Seitz, et al., filed Sep. 14, 2010, United States Patent Office, Alexandria, VA (United States) (Not Published).

Copending U.S. Appl. No. 12/936,700, inventors Andersch, et al., Int'l Filing Date of Apr. 7, 2009, United States Patent Office, Alexandria, VA (United States) (Not Published).

Copending U.S. Appl. No. 12/915,222, inventors Cristau, et al., filed Oct. 29, 2010, United States Patent Office, Alexandria, VA (United States) (Not Published).

Copending U.S. Appl. No. 13/055,374, inventors Vermeer, et al., Int'l Filing Date of Jul. 11, 2009, United States Patent Office, Alexandria, VA (United States) (Not Published).

Copending U.S. Appl. No. 11/921,667, inventors Stenzel, et al., Int'l Filing Date of May 27, 2006, United States Patent Office, Alexandria, VA (United States) (Not Published).

Prosecution History of European Patent Appl. No. 03735610.2 (European Counterpart of U.S. Appl. No. 10/518,742), Jul. 13, 2006—Sep. 25, 2009.

Partial English language translation of Prosecution History of European Patent Appl. No. 03735610.2, Jul. 13, 2006-Sep. 25, 2009.

Opposition Proceeding in European Patent No. EP-B-1482798, Mar. 5, 2007-Nov. 9, 2009.

Partial English language translation of Opposition Proceeding in European Patent No. EP-B-1482798, Feb. 26, 2007-Nov. 9, 2009.

Tomlin, C., ed, *The Pesticide Manual*, 1242-1245, British Crop Protection Council, Farnham, UK (1997).

"Metominostrobin data sheet," Compendium of Pesticide Common Names, accessed at. http://www.alanwood.net/pesticides/metominostrobin.html, accessed on Apr. 8, 2009, 1 page.

"Azoxystrbin data sheet," Compendium of Pesticide Common Names, accessed at http://www.alanwood.net/pesticides/azoxystrobin.html, accessed on Apr. 8, 2009, 1 page.

"Kresoxim-methyl data sheet," Compendium of Pesticide Common Names, accessed at http:///www.alanwood.net/pesticides/kresoxim-methyl.html, accessed on Apr. 8, 2009, 1 page.

\* cited by examiner

USE OF ALKYL CARBOXYLIC ACID AMIDES AS PENETRATION ENHANCERS

The invention relates to the use of N-monoalkyl- and N,N-dialkyl-alkylcarboxamides in plant protection compositions and plant protection compositions comprising such compounds.

EP-A 0 453 899 discloses the use of N,N-dimethyl-$C_5$-$C_{19}$-alkylcarboxamides as crystallization inhibitors for certain azole fungicides, such as tebuconazole, which have a tendency to crystallize.

Surprisingly, it has now been found that alkylcarboxamides are suitable for increasing the penetration of agrochemical active substances across the cuticle of the plant and therefore for increasing the biological activity of plant protection compositions.

The present invention therefore relates to the use of carboxamides of the formula (I)

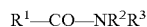
(I)

in which
$R^1$ represents $C_3$-$C_{19}$-alkyl,
$R^2$ represents $C_1$-$C_6$-alkyl and
$R^3$ represents H or $C_1$-$C_6$-alkyl
for promoting the penetration of agrochemical active substances into plants.

$R^1$ is preferably an unbranched or branched, saturated or unsaturated, especially preferably unbranched, saturated alkyl group having 5 to 11 carbon atoms, very especially preferably n-heptyl or n-nonyl.

$R^2$ and $R^3$ are preferably identical or different, especially preferably identical, and an unbranched or branched, especially preferably unbranched alkyl group having 1 to 4 carbon atoms, very especially preferably methyl.

Especially preferred compounds of the formula (I) are therefore those of the formula (Ia)

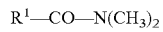
(Ia)

in which
$R^1$ has the abovementioned meanings.

The following are very especially preferred: N,N-dimethyl-n-hexanamide, N,N-dimethyl-n-octanamide, N,N-dimethyl-n-decanamide and N,N-dimethyl-n-dodecanamide, in particular N,N-dimethyl-n-octanamide and N,N-dimethyl-n-decanamide.

The compounds of the formula (I) are employed individually or in the form of mixtures. Preferred is not only the use of individual active substances but also the use of a mixture which is known under the trade names Hallcomid, Genagen or Agnique and which consists on average of 5% (unless otherwise specified, all percentages are percent by weight) N,N-dimethyl-hexanamide, 50% N,N-dimethyl-octanamide, 40% N,N-dimethyl-decanamide and 5% N,N-dimethyl-dodecanamide.

The acid amides of the formula (I) are known and commercially available.

The amount of one or more compounds of the formula (I) for the use according to the invention in plant protection compositions can vary within wide limits, depending on the active substance and the formulation type.

In a preferred embodiment, the acid amides of the formula (I) thus additionally act as solvents, while in another, likewise preferred embodiment, they act as additives for improving the biological activity. A further possibility is also the use as a tank mix additive, i.e. the addition to the spray mixture of the formulation and not as integral component of the formulation, and the use of the formulation as mixing partner for improving the biological activity of other agents as the result of an enhanced penetration.

Plant protection compositions according to the invention, i.e. plant protection compositions which, in accordance with the invention, comprise one or more acid amides (I) for increasing the penetration of the active substance into plants, preferably have the following composition:
1 to 90%, especially preferably 5 to 50%, of one or more agrochemical active substances,
1 to 90%, especially preferably 5 to 70%, of one or more acid amides of the formula (I) and
0 to 98% of other additives.

If the acid amides of the formula (I) do not act as solvents, but as pure additives for promoting the penetration of active substances into plants, they are preferably present in the plant protection compositions according to the invention in an amount of from 1 to 30%, especially preferably from 5 to 20%, in particular from 5 to 10%.

Since the mechanism of action of the acid amides (I) as penetrants is intrinsically independent of the nature of the agrochemical active substance employed, it is possible to use all active substances whose biological activity can be increased as the result of an enhanced penetration into a crop plant or a harmful plant.

The following may be mentioned by preference: fungicides, bactericides, insecticides, acaricides, nematicides, herbicides, plant growth regulators, plant nutrients, repellents with systemic properties, and contact-acting agents which are suitable as combination partners.

Furthermore preferred are systemic active substances, i.e. those which are taken up by the plant via the leaves or the roots and which are translocated in the sap, the plant's transport system. Especially preferred active substances are those with a log P value of $\leq 4$ (determined as specified in EC Directive 79/831 Annex V. A8 by HPLC, gradient method, acetonitrile/0.1% aqueous phosphoric acid), in particular those with a log P value of $\leq 4$ and $\geq 0.1$.

Examples of individual active substances are:
Fungicides:
2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benalaxyl-M; benodanil; benomyl; benthiavalicarb-isopropyl; benzamacril; benzamacril-isobutyl; bilanafos; bina-pacryl; biphenyl; bitertanol; blasticidin-S; boscalid; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; dinicon-azole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb;

irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrine; quinconazole; quinoxyfen; quintozene; silthiofam; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxy-phenyl]ethyl]-3-methyl-2-[(methylsulfonyl)amino]butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-6-methoxy-3-pyridinyl)cyclopropanecarboxamide; N-butyl-8-(1,1-dimethylethyl)-1-oxaspiro[4,5]decan-3-amine; sodium tetracarbonate; N-3'4'-dichloro-5-fluorobiphenyl-2-yl)-3-(difluoromethyl)-1-methyl-1H-pyrazole-4-carboxamide; and copper salts and preparations, such as Bordeaux mixture; copper hydroxide, copper naphthenate; copper oxychloride; copper sulphate; cufraneb; cuprous oxide; mancopper; oxine copper.

Bactericides:
bronopol, dichlorophen, nitrapyrin, nickel-dimethyldithiocarbamate, kasugamycin, octhilinone, furancarboxylic acid, oxytetracyclin, probenazole, streptomycin, tecloftalam, copper sulphate and other copper preparations.

Insecticides/Acaridices/Nematicides:
1. Acetylcholinesterase (AChE) inhibitors
1.1 carbamates (for example alanycarb, aldicarb, aldoxycarb, allyxycarb, aminocarb, azamethiphos, bendiocarb, benfuracarb, bufencarb, butacarb, butocarboxim, butoxycarboxim, carbaryl, carbofuran, carbosulfan, chloethocarb, coumaphos, cyanofenphos, cyanophos, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, triazamate, trimethacarb, XMC, xylylcarb)
1.2 organophosphates (for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methyl sulphone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion)

2. Sodium Channel Modulators/Voltage-Dependent Sodium Channel Blockers
2.1 pyrethroids (for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cyproprothrin, cyflu-thrin, cyhalothrin, cypermethrin (alpha-, beta-, theta-, zeta-), cyphenothrin, DDT, deltamethrin, empenthrin (1R isomer), esfenvalerate, etofenprox, fenfluthrin, fenpropathrin, fenpyrithrin, fen-valerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralomethrin, transfluthrin, ZXI 8901, pyrethrins (pyrethrum))
2.2 oxadiazines (for example indoxacarb)

3. Acetylcholine Receptor Agonists/Antagonists
3.1 Chloronicotinyls/neonicotinoids (for example acetamiprid, clothianidin, dinotefuran, imidacloprid, nitenpyram, nithiazine, thiacloprid, thiamethoxam)
3.2 nicotine, bensultap, cartap 4. Acetylcholine Receptor Modulators
4.1 spinosyns (for example spinosad)

5. GABA-Controlled Chloride Channel Antagonists
5.1 cyclodiene organochlorines (for example camphechlor, chlordane, endosulfan, gamma-HCH, HCH, heptachlor, lindane, methoxychlor)
5.2 fiprols (for example acetoprole, ethiprole, fipronil, vaniliprole)

6. Chloride Channel Activators
6.1 mectins (for example abamectin, avermectin, emamectin, emamectin-benzoate, ivermectin, milbemectin, milbemycin)

7. Juvenile Hormone Mimetics
(for example diofenolan, epofenonane, fenoxycarb, hydroprene, kinoprene, methoprene, pyriproxifen, triprene)

8. Ecdysone Agonists/Disruptors
8.1 diacylhydrazines (for example chromafenozide, halofenozide, methoxyfenozide, tebufenozide)

9. Chitin Biosynthesis Inhibitors
9.1 benzoylureas (for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron)
9.2 buprofezin
9.3 cyromazine 10. Inhibitors of Oxidative Phosphorylation, ATP Disruptors
10.1 diafenthiuron
10.2 organotin compounds (for example azocyclotin, cyhexatin, fenbutatin-oxide)

11. Uncoupler of Oxidative Phosphorylation by Interrupting the H Proton Gradient
11.1 pyrroles (for example chlorfenapyr)
11.2 dinitrophenols (for example binapacyri, dinobuton, dinocap, DNOC)

12. Site-I Electron Transport Inhibitors
12.1 METIs (for example fenazaquin, fenpyroximate, pyrimidifen, pyridaben, tebufenpyrad, tolfenpyrad)
12.2 hydramethylnon
12.3 dicofol
13. Site-II Electron Transport Inhibitors
13.1 rotenone
14. Site-III Electron Transport Inhibitors
14.1 acequinocyl, fluacrypyrim
15. Microbial Disruptors of the Insect Gut Membrane
*Bacillus thuringiensis* strains
16. Fat Synthesis Inhibitors
16.1 tetronic acids (for example spirodiclofen, spiromesifen)
16.2 tetramic acids [for example 3-(2,5-dimethylphenyl)-8-methoxy-2-oxo-1-azaspiro[4,5]dec-3-en-4-yl ethyl carbonate (also known as: carbonic acid, 3-(2,5-dimethylphenyl)-8-methoxy-2-oxo-1-azaspiro[4,5]dec-3-en-4-yl ethyl ester, CAS-Reg. No.: 382608-10-8) and carbonic acid, cis-3-(2,5-dimethylphenyl)-8-methoxy-2-oxo-1-azaspiro[4.5]dec-3-en-4-yl ethyl ester (CAS-Reg. No.: 203313-25-1)]
17. Carboxamides
(for example flonicamid)
18. Octopaminergic Agonists
(for example amitraz)
19. Inhibitors of Magnesium-Stimulated ATPase
(for example propargite)
20. Phthalamides
(for example $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (CAS-Reg. No.: 272451-65-7), flubendiamide)
21. Nereistoxin Analogues
(for example thiocyclam hydrogen oxalate, thiosultap-sodium)
22. Biologicals, Hormones or Pheromones
(for example azadirachtin, *Bacillus* spec., *Beauveria* spec., codlemone, *Metarrhizium* spec., *Paecilomyces* spec., thuringiensin, *Verticillium* spec.)
23. Active Compounds with Unknown or Unspecific Mechanisms of Action
23.1 fumigants (for example aluminium phosphide, methyl bromide, sulphuryl fluoride)
23.2 selective antifeedants (for example cryolite, flonicamid, pymetrozine)
23.3 mite growth inhibitors (for example clofentezine, etoxazole, hexythiazox)
23.4 amidoflumet, benclothiaz, benzoximate, bifenazate, bromopropylate, buprofezin, quinomethionate, chlordimeform, chlorobenzilate, chloropicrin, clothiazoben, cycloprene, cyflu-metofen, dicyclanil, fenoxacrim, fentrifanil, flubenzimine, flufenerim, flutenzin, gossyplure, hydra-methylnone, japonilure, metoxadiazone, petroleum, piperonyl butoxide, potassium oleate, pyrafluprole, pyridalyl, pyriprole, sulfluramid, tetradifon, tetrasul, triarathene, verbutin,
furthermore the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo isomer (CAS-Reg. No. 185984-60-5) (cf. WO 96/37494, WO 98/25923), and preparations which contain insecticidally active plant extracts, nematodes, fungi or viruses.
Herbicides:
Anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluoroxypyr, MCPA, MCPP and triclopyr; aryloxyphenoxy-alkanoic esters, such as, for example, diclofop-methyl, fenoxaprop-ethyl, fluazifop-butyl, haloxyfop-methyl and quizalofop-ethyl; azinones, such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thio-bencarb and tri-allate; triazines such as, for example, atrazin, cyanazin, simazin, simetryne, terbutryne and terbutylazin; triazinones such as, for example, hexazinon, metamitron and metribuzin; others such as, for example, aminotriazole, 4-amino-N-(1,1-dimethylethyl)-4,5-dihydro-3-(1-methylethyl)-5-oxo-1H-1,2,4-triazole-1-carboxamide, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Examples of plant growth regulators which may be mentioned are chlorcholin chloride, thidiazuron, cyclanilide, ethephon, benzyladenine and gibberellic acid, and examples of the safener groups which may be mentioned are mefenpyr, isoxadifen and cloquintocet-mexyl.

Examples of plant nutrients which may be mentioned are conventional inorganic or organic fertilizers for providing plants with macronutrients and/or micronutrients.

Examples of repellents which may be mentioned are diethyltolylamide, ethylhexanediol and butopyronoxyl.

Preferred examples of fungicides are the strobilurin fungicides such as, for example,

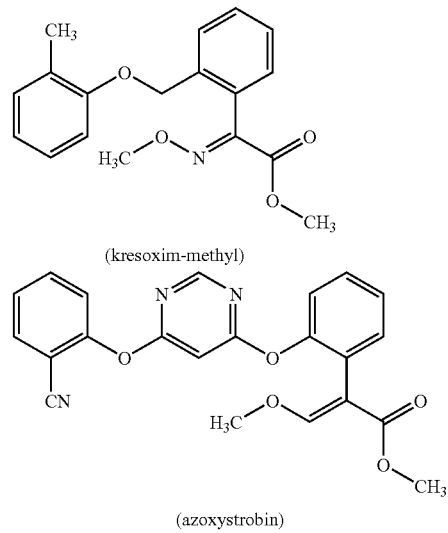

(kresoxim-methyl)

(azoxystrobin)

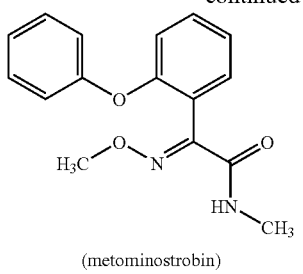
(metominostrobin)
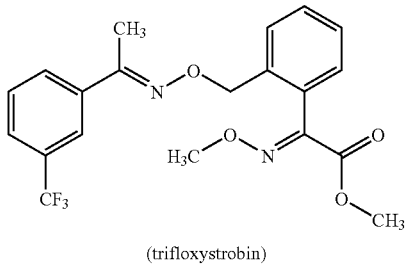
(trifloxystrobin)
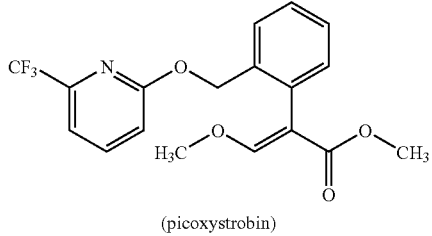
(picoxystrobin)
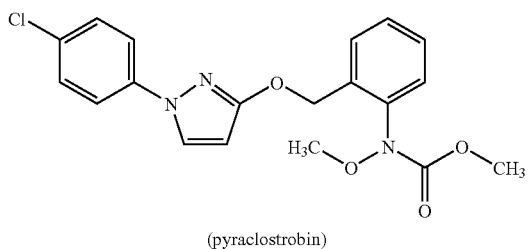
(pyraclostrobin)
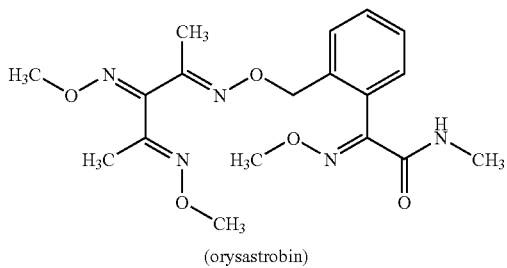
(orysastrobin)
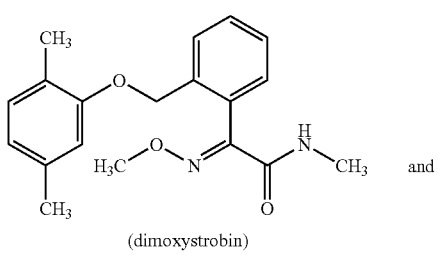 and
(dimoxystrobin)
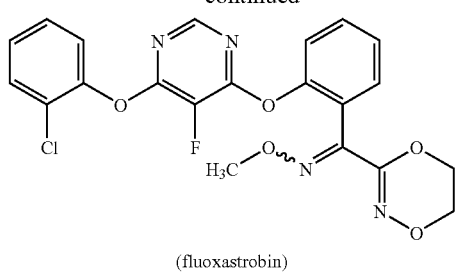
(fluoxastrobin)
And the azole fungicides such as
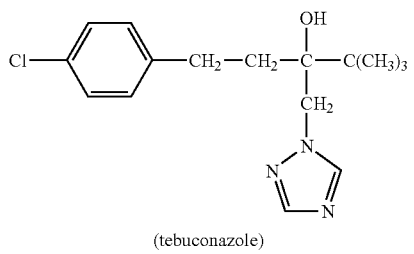
(tebuconazole)
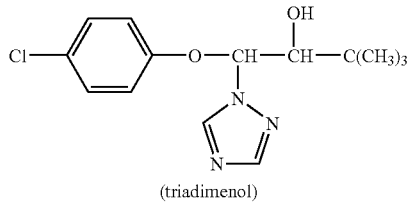
(triadimenol)
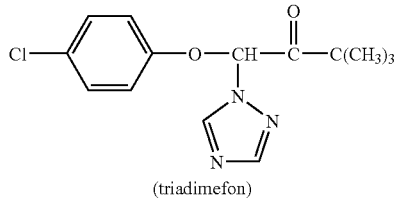
(triadimefon)
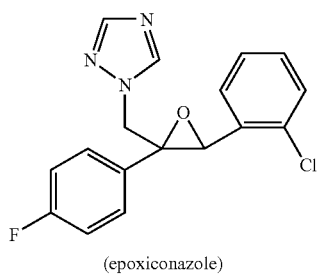
(epoxiconazole)
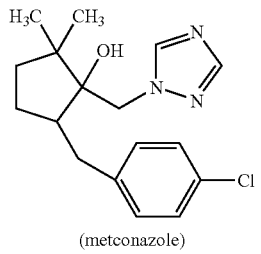
(metconazole)

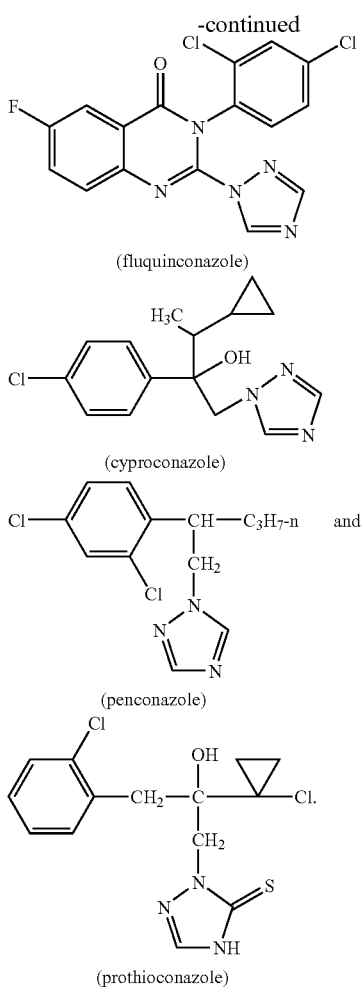

(fluquinconazole)

(cyproconazole)

(penconazole)

(prothioconazole)

Preferred examples of fungicides which may be mentioned are prothioconazole, fluoxastrobin, trifloxystrobin, spiroxamine and tebuconazole.

Prothioconazole is especially preferred, if appropriate as a mixture with one or more of the following active substances: spiroxamine, tebuconazole, fluoxastrobin, trifloxystrobin.

The formulation types which are suitable include all formulations which are applied to plants or their propagation material. The methods used for preparing them are generally known to the skilled worker and for example described in Winnacker-Küchler, "Chemische Technologie" [Chemical Technology], volume 7, C. Hanser Verlag Munich, 4th edition, 1986; J. W. van Valkenburg, "Pesticide Formulations", Marcel Dekker N.Y., 1973, K. Martens, "Spray Drying Handbook", 3rd Ed. 1979, G. Goodwin Ltd., London, or Mollet, Grubenmann, "Formulierungstechnik" [Formulation Technology], Wiley-VCH-Verlag, Weinheim, 2000.

Examples of formulation types are all those mentioned in the "Manual on development and use of FAO and WHO specifications for pesticides" (FAO and WHO, 2002, appendix E) (in each case using the GCPF formulation codes with English abbreviation and name): AB Grain bait; AE Aerosol dispenser; AL Any other liquid; AP Any other powder; CF Capsule Suspension for Seed Treatment; CG Encapsulated granule; CL Contact liquid or gel; CP Contact powder; CS Capsule suspension; DC Dispersible concentrate; DP Dustable powder; DS Powder for dry seed treatment; DT Tablet for direct application; EC Emulsifiable concentrate; ED Electrochargeable liquid; EG Emulsifiable Granule; EO Emulsion, water in oil; EP emulsifiable powder, ES Emulsion for seed treatment; EW Emulsion, oil in water; FG Fine granule; FS Flowable concentrate for seed treatment; GF Gel for Seed Treatment; GG Macrogranule; GL Emulsifiable gel; GP Flodust; GR Granule; GS Grease; GW Water soluble gel; HN Hot fogging concentrate; KK Combi-pack solid/liquid; KL Combi-pack liquid/liquid; KN Cold fogging concentrate; KP Combi-pack solid/solid; LA Lacquer; LS Solution for seed treatment; ME Microemulsion; MG Microgranule; OD oil dispersion, OF-Oil miscible flowable concentrate/oil miscible suspension; OL Oil miscible liquid; OP Oil dispersible powder; PA Paste; PC Gel or paste concentrate; PO Pour-on; PR Plant rodlet; PS Seed coated with a pesticide; PT Pellet; RB Bait (ready for use); SA Spot-on; SC suspension concentrate, SD suspension concentrate for direct application, SE Suspo-emulsion; SG Water soluble granule; SL Soluble concentrate; SO Spreading oil; SP Water soluble powder; SS Water soluble powder for seed treatment; ST Water soluble tablet; SU Ultra-low volume (ULV) suspension; TB Tablet; TC Technical material; TK Technical concentrate; UL Ultra-low volume (ULV) liquid; VP Vapour releasing product; WG Water dispersible granules; WP Wettable powder; WS Water dispersible powder for slurry seed treatment; WT Water dispersible tablet; XX Others.

Liquid formulation types are preferred. These include the formulation types DC (GCPF formulation code for dispersible concentrate); EC (GCPF formulation code for emulsion concentrate); EW (GCPF formulation code for oil-in-water emulsion); ES (GCPF formulation code for emulsion for seed treatment), FS (GCPF formulation code for multiphase concentrate for seed treatment), EO (GCPF formulation code for water-in-oil emulsion; ME (GCPF formulation code for microemulsion; SE (GCPF formulation code for suspo-emulsion); SL (GCPF formulation code for soluble concentrate); CS (GCPF formulation code for capsule suspension) and AL (GCPF formulation code for ready-to-use liquid formulation, any other liquids for undiluted use).

Emulsion concentrates (formulation type EC) are especially preferred.

Suitable additives which may be present in the formulations according to the invention, preferably the liquid formulations according to the invention, are all customary formulation adjuvants such as organic solvents, antifoams, emulsifiers, dispersants, preservatives, acids and bases, colorants, fillers and also water.

Antifoams which are suitable are conventional antifoams which are present in formulations of agrochemical active substances. Examples which may be mentioned are silicone oils, silicone oil dispersions, magnesium stearate, phosphinic and phosphonic acids, in particular Fluowet PL 80®.

Suitable organic solvents are not only alkanecarboxamides, such as those of the formula (I), but also all customary organic solvents which thoroughly dissolve the agrochemically active substances employed. The following may be mentioned as being preferred: aliphatic and aromatic, optionally halogenated hydrocarbons such as toluene, xylene, Solvesso®, mineral oils such as white spirit, petroleum, alkylbenzenes and spindle oil, furthermore tetrachloromethane, chloroform, methylene chloride and dichloromethane, and furthermore esters such as ethyl acetate, lactates, furthermore lactones such as butyrolactone, moreover lactams such as N-methylpyrrolidone, N-octylpyrrolidone, N-dodecylpyrrolidone, N-octylcaprolactam and N-methylcaprolactam, γ-butyrolactone, dimethylformamide and tributyl phosphate.

Preference is given to carboxamides of the formula (I). Especially preferred are N,N-dimethyl-n-octanamide and N,N-dimethyl-n-decanamide and their mixtures.

Suitable emulsifiers are conventionally used surface-active substances which are present in formulations of agrochemically active substances. Examples which may be mentioned are ethoxylated nonylphenols, polyethylene glycol ethers of linear alcohols, end-capped and non-end-capped alkoxylated linear and branched, saturated and unsaturated alcohols, reaction products of alkylphenols with ethylene oxide and/or propylene oxide, ethylene oxide/propylene oxide block copolymers, polyethylene glycols and polypropylene glycols, furthermore fatty acid esters, end-capped and non-end-capped alkoxylated linear and branched, saturated and unsaturated fatty acids, fatty acid polyglycol ether esters, alkylsulphonates, alkyl sulphates, aryl sulphates, ethoxylated arylalkylphenols such as, for example tristyryl phenol ethoxylate with an average of 16 ethylene oxide units per molecule, furthermore ethoxylated and propoxylated arylalkylphenols and sulphated or phosphated arylalkylphenol ethoxylates or -ethoxy- and -propoxylates. Especially preferred are tristyrylphenol alkoxylates and fatty acid polyglycol ether esters. Very especially preferred are tristyrylphenol ethoxylates, tristyrylphenol ethoxy-propoxylates and castor oil polyglycol ether esters, in each case individually or in mixtures. If appropriate, additives such as surfactants or esters of fatty acids which contribute to improving the biological activity may also be used.

Dispersants which can be used are all substances which are conventionally employed in plant protection compositions for this purpose. In addition to the examples which are mentioned hereinabove as emulsifiers, the following may be mentioned by preference: natural and synthetic, water-soluble polymers such as gelatin, starch and cellulose derivatives, in particular cellulose esters and cellulose ethers, furthermore polyvinyl alcohol, polyvinylpyrrolidone, polyacrylic acid, polymethacrylic and copolymers of (meth)acrylic acid and (meth)acrylic esters, and furthermore alkali-metal-hydroxide-neutralized copolymers of methacrylic acid and methacrylic esters.

Preservatives which can be used are all substances which are conventionally present in plant treatment compositions for this purpose. Examples which may be mentioned are Preventol® and Proxel®.

Colorants which are suitable are all inorganic or organic colorants which are conventionally used for the preparation of plant protection compositions. Examples which may be mentioned are titanium dioxide, carbon black, zinc oxide and blue pigments.

Fillers which are suitable are all substances which are conventionally employed in plant protection compositions for this purpose. The following may be mentioned by preference: inorganic particles, such as carbonates, silicates and oxides with a mean particle size of from 0.005 to 5 µm, especially preferably from 0.02 to 2 µm. Examples which may be mentioned are silicon dioxide, what are known as highly dispersed silica, silica gels, and natural and synthetic silicates and alumosilicates.

Suitable compounds which act as emulsion stabilizers and/or crystallization inhibitors are all substances which are conventionally employed in plant protection compositions for this purpose.

The content of the individual components in the formulations according to the invention can be varied within a substantial range.

The preparation of the formulations according to the invention is accomplished for example in such a manner that the components are mixed with one another in the described ratios. If the agrochemical active substance is a solid, the latter is generally employed in finely ground form or in the form of a solution or suspension in an organic solvent or water. If the agrochemical active substance is liquid, the use of an organic solvent can frequently be dispensed with. Moreover, a solid agrochemical substance may be employed in the form of a melt.

When carrying out the process, the temperatures can be varied within a certain range. In general, the process is carried out at temperatures of between 0° C. and 80° C., preferably between 10° C. and 60° C.

When carrying out the process according to the invention, a procedure is generally followed in which the acid amides (I) are mixed with one or more active substances and, if appropriate, with additives. The components can be mixed with one another in any order.

The equipment which is suitable for carrying out the process according to the invention is customary equipment which is employed for the preparation of agrochemical formulations.

Suitable application forms are all those methods which are known to the skilled worker as being conventionally used; examples which may be mentioned are: spraying, immersion, misting and a series of specific methods for the direct below- or above-ground treatment of whole plants or parts (seeds, root, stolons, stalks, stem, leaf), such as, for example, in the case of trees the injection into the stem or in the case of perennial plants stalk bands, and a series of specific indirect application methods.

The specific application rate of the plant protection compositions of a wide range of formulation types for controlling the abovementioned harmful organisms, either based on area and/or the object to be treated varies greatly. In general, the application media which are known to the skilled worker as being conventionally used for the field of application in question, are employed in customary amounts, such as, for example, from several hundred liters of water per hectare in the case of standard spray methods to a few liters of oil per hectare in the case of 'Ultra Low Volume' aerial application to a few milliliters of a physiological solution in the case of injection methods. The concentrations of the plant protection compositions according to the invention in the relevant application media therefore vary within a wide range and depend on the specific field of application. In general, concentrations are used which are known to the skilled worker as being conventionally used for the specific field of application. Preferred concentrations are from 0.01% by weight to 99% by weight, especially preferred concentrations from 0.1% by weight to 90% by weight.

The agrochemical formulations according to the invention, for example in the use forms which are conventional for liquid preparations, can be applied either as such or after previously having been diluted with water, that is to say for example as emulsions, suspensions or solutions. The application here is accomplished by the customary methods, that is to say, for example, by spraying, pouring or injecting.

The application rate of the agrochemical formulations according to the invention can be varied within a substantial range. It depends on the agrochemical active substances in question and on their content in the formulations.

The invention furthermore relates to a method of promoting the penetration of agrochemical active substances into plants, the agrochemical active substance being applied to the plants either simultaneously or sequentially with one or more acid amides of the formula (I).

Some of the plant protection compositions according to the invention are known and some are new.

The invention also relates to a plant protection composition comprising a) 1 to 80% of one or more acid amides of the formula (I) as stated above, b) 1 to 90% of one or more agrochemical active substances and c) 0 to 98% of additives, the following agrochemical substances being excluded:

A. an azole derivative of the formula (II)

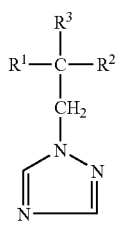

(II)

in which a) $R^1$ represents

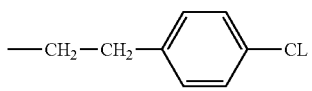

$R^2$ represents tert-butyl and $R^3$ represents hydroxyl, or b) $R^1$ represents 4-fluorophenyl, $R^2$ represents 2-fluorophenyl and $R^3$ represents hydroxyl, or c) $R^1$ represents 2,4-dichlorophenyl, $R^2$ represents n-butyl and $R^3$ represents hydroxyl, or d) $R^1$ represents

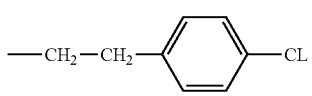

$R^2$ represents phenyl and $R^3$ represents cyano, or e) $R^1$ represents 2-chlorobenzyl, $R^2$ represents 1-chlorocycloprop-1-yl and $R^3$ represents hydroxyl, or f) $R^1$ represents 4-chlorophenyl $R^2$ represents

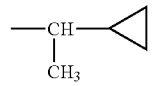

and $R^3$ represents hydroxyl, and/or an azole derivative of the formula (III)

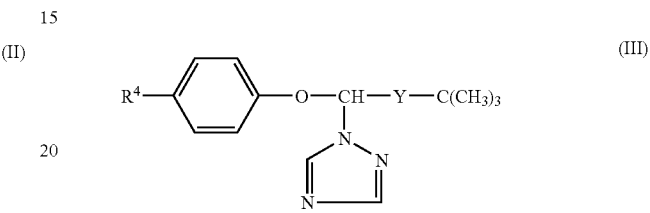

(III)

in which a) Y represents —CH(OH) and $R^4$ represents chlorine or phenyl, or b) Y represents CO and $R^4$ represents chlorine, and/or an azole derivative of the formula (IV)

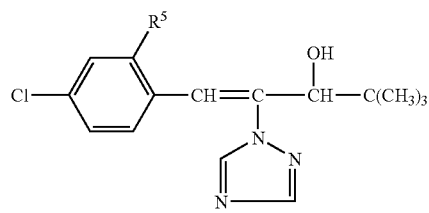

(IV)

in which $R^5$ represents hydrogen or chlorine, and/or

1-[bis(4-fluorophenyl)methylsilyl]-1H-(1,2,4-triazole) of the formula (V),

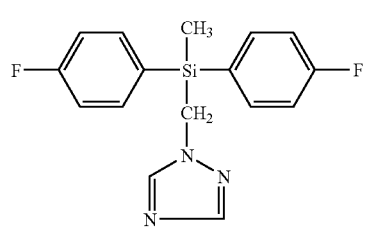

(V)

B. a carbamate of the formula (VI)

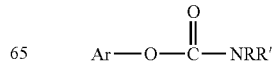

where
Ar represents an aryl group or a heterocyclic group, each of which is optionally substituted,
and
R, R' represent H or methyl; and
C. thiadiazuron.

The invention also relates to a plant protection composition comprising
a) 1 to 30%, preferably 5 to 20%, especially preferably 5 to 10%, of one or more acid amides of the formula (I) as stated above,
b) 1 to 90% of one or more agrochemical active substances and
c) 0 to 98% of additives,
excluding tebuconazole and triadimenol as agrochemical active substances.

Preferred plant protection compositions according to the invention are those which comprise prothioconazole as agrochemical active substance, if appropriate in mixture with further agrochemical active substances.

As regards the use of herbicides, the plants treated in accordance with the invention are all weed species. As regards the protection of crop plants by the application of, for example, fungicides and insecticides, the use in economically important, including, for example, transgenic, crops of useful plants and ornamentals, for example cereals such as wheat, barley, rye, oats, sorghum and millet, rice, cassava and maize, or else crops of peanut, sugar beet, cotton, soya, oilseed rape, potato, tomato, pea and vegetables is preferred.

The invention is illustrated in greater detail by the examples without being limited thereto.

EXAMPLES

Penetration Test

In this test, the measured quantity was the penetration of active substances across enzymatically isolated cuticles of apple tree leaves.

The leaves used were leaves which had been excised in the fully developed state from cv. Golden Delicious. The cuticles were isolated in such a way that
first, using the vacuum infiltration method, leaf discs which had been marked with dye and punched from the underside were filled with a pectinase solution (0.2 to 2% strength) which had been buffered to a pH of between 3 and 4,
then, sodium azide was added and
the leaf discs treated thus were left to stand until the original leaf structure had disintegrated and the noncellular cuticle had detached itself.

Thereafter, only the cuticles of the upper side of the leaf which were free from stomata and hairs were used. They were washed repeatedly, alternating with water and a buffer solution of pH 7. The resulting clean cuticles were finally applied to Teflon discs and smoothed and dried using a weak stream of air.

In the next step, the cuticle membranes obtained were placed into stainless-steel diffusion cells (=transport chambers) in order to carry out membrane transport studies. To this end, tweezers were used to place the cuticles centrally on the edges of the diffusion cells which had been painted with silicone fat and sealed using a ring, which had also been painted with fat. The arrangement had been chosen in such a way that the morphological external side of the cuticles was directed outwardly, that is to say facing the air, while the original internal side faced the inside of the diffusion cell. The diffusion cells were filled with water or with a mixture of water and solvent.

To determine the penetration, in each case 9 µl of a spray mixture of the composition mentioned in the examples were applied to the external side of a cuticle.

In the spray mixtures, CIPAC water was used in each case.

After the spray mixtures had been applied, the water was left to evaporate in each case, and the chambers were then inverted and placed into temperature-controlled cans, the external side of the cuticle being flushed with air at a defined temperature and humidity. The beginning of the penetration therefore took place at a relative atmospheric humidity of 60% and a set temperature of 25° C. The penetration of the active substance was measured using a radiolabelled active substance.

As can be seen with reference to the examples in the table, the presence of acid amides (in the present case N,N-dimethyldecanamide by way of example) gives rise to a substantially increased uptake in comparison with the formulations which lack the acid amides. The employed alternatives to the acid amide are examples of commercially available solvents for formulations.

Table, Example 1

The active substance is dissolved in an acetone/water mixture at a concentration of 0.5 g/l, and the penetration is measured after 3 and 48 hours.

Table, Example 2

The water is mixed together with formulation adjuvants and N,N-dimethyldecanamide and this mixture is diluted with water so that the dilution again contains an active substance concentration of 0.5 g/l. As in Ex. 1, the penetration was then measured after 3 and 48 hours.

Table, Example 3

The active substance is mixed together with formulation adjuvants and N-methylpyrrolidone and this mixture is diluted with water so that the dilution contains an active substance concentration of 0.5 µl. The penetration was measured after 3 and 48 hours.

Table, Example 4

The active substance is mixed together with formulation adjuvants and γ-butyrolactone and this mixture is diluted with water so that the dilution contains an active substance concentration of 0.5 g/l. The penetration was measured after 3 and 48 hours.

Table, Example 5

The active substance is mixed together with formulation adjuvants and N,N-dimethyldecanamide and this mixture is diluted with water so that the dilution contains an active substance concentration of 1.0 µl. As in Ex. 1, the penetration was then measured after 3 and 48 hours.

Table, Example 6

The active substance is mixed together with formulation adjuvants and N-methylpyrrolidone and this mixture is diluted with water so that the dilution contains an active substance concentration of 1.0 g/l. The penetration was measured after 3 and 48 hours.

Table, Example 7

The active substance is mixed together with formulation adjuvants and γ-butyrolactone and this mixture is diluted with water so that the dilution contains an active substance concentration of 1.0 g/l. The penetration was measured after 3 and 48 hours.

Table, Example 8

The active substances prothioconazole and tebuconazole are mixed together with formulation adjuvants and N,N-dimethyldecanamide and this mixture is diluted with water so that the dilution contains a prothioconazole concentration of 0.5 g/l. The penetration was then measured after 3 and 48 hours.

Table, Example 9

The active substances prothioconazole and tebuconazole are mixed together with formulation adjuvants and N-methylpyrrolidone and this mixture is diluted with water so that the dilution contains a prothioconazole concentration of 0.5 g/l. The penetration was then measured after 3 and 48 hours.

Table, Example 10

The active substances prothioconazole and tebuconazole are mixed together with formulation adjuvants and γ-butyrolactone and this mixture is diluted with water so that the dilution contains a prothioconazole concentration of 0.5 g/l. The penetration was then measured after 3 and 48 hours.

Table, Example 11

The active substances prothioconazole and spiroxamine are mixed together with formulation adjuvants and N,N-dimethyldecanamide and this mixture is diluted with water so that the dilution contains a prothioconazole concentration of 0.5 g/l. The penetration was measured after 3 and 48 hours.

Table, Example 12

The active substances prothioconazole and spiroxamine are mixed together with formulation adjuvants and N-methylpyrrolidone and this mixture is diluted with water so that the dilution contains a prothioconazole concentration of 0.5 µl. The penetration was measured after 3 and 48 hours.

Table, Example 13

The active substances prothioconazole and spiroxamine are mixed together with formulation adjuvants and a mixture of aromatics (boiling point 220-290° C.) and this mixture is diluted with water so that the dilution contains a prothioconazole concentration of 0.5 g/l. The penetration was measured after 3 and 48 hours.

| Penetration test, table | | | | | |
|---|---|---|---|---|---|
| Example | Solvent | Active substances | Prothioconazole concentration (g/l) in the aqueous dilution | % penetration (+/−SE) prothioconazole after 3 h n = 5-7 | % penetration (+/−SE) prothioconazole after 48 h n = 5-7 |
| 1 | Acetone (without further formulation adjuvants) | prothioconazole | 0.5 | 0.23 (0.06) | 0.72 (0.17) |
| 2 | N,N-Dimethyldecanamide | prothioconazole | 0.5 | 1.73 (0.45) | 6.99 (1.23) |
| 3 | N-Methylpyrrolidone | prothioconazole | 0.5 | 0.16 (0.04) | 2.23 (0.49) |
| 4 | gamma-Butyrolactone | prothioconazole | 0.5 | 0.12 (0.04) | 1.4 (0.37) |
| 5 | N,N-Dimethyldecanamide | prothioconazole | 1.0 | 1.24 (0.34) | 6.82 (1.63) |
| 6 | N-Methylpyrrolidone | prothioconazole | 1.0 | 0.18 (0.03) | 1.57 (0.45) |
| 7 | gamma-Butyrolactone | prothioconazole | 1.0 | 0.09 (0.03) | 2.38 (1.29) |
| 8 | N,N-Dimethyldecanamide | prothioconazole & tebuconazole | 0.5 | 13.13 (1.96) | 38.17 (6.78) |
| 9 | N-Methylpyrrolidone | prothioconazole & tebuconazole | 0.5 | 0.74 (0.12) | 13.42 (1.36) |
| 10 | gamma-Butyrolactone | prothioconazole & tebuconazole | 0.5 | 0.67 (0.19) | 13.9 (2.48) |
| 11 | N,N-Dimethyldecanamide | prothioconazole & spiroxamine | 0.5 | 8.08 (1.01) | 28.69 (3.51) |
| 12 | N-Methylpyrrolidone | prothioconazole & spiroxamine | 0.5 | 1.62 (0.28) | 17.79 (3.7) |
| 13 | Mixture of aromatics(*1) | prothioconazole & spiroxamine | 0.5 | 0.84 (0.3) | 10.15 (4.59) |
| Example | Test substance (g/l) | Active substances | Thidiazuron concentration (g/l) in the dilution (acetone/water, 20/80) | % penetration thidiazuron after 1-1.5 h n = 5-7 | % penetration thidiazuron after 22 h n = 5-7 |
| 14 | Active substance (without test substance) | thidiazuron | 0.5 | <1 | <1 |
| 15 | N,N-Dimethyloctanamide/decanamide**(3 g/l) | thidiazuron | 0.5 | 37.7 | 43.1 |
| 16 | Hasten*** (2 g/l) | thidiazuron | 0.5 | 8.0 | 27.0 |
| 17 | Hasten (10 g/l) | thidiazuron | 0.5 | 12.6 | 39.2 |
| 18 | Agridex**** (10 g/l) | thidiazuron | 0.5 | 1.44 | 46.6 |

| Penetration test, table | | | | | |
|---|---|---|---|---|---|
| Example | Formulation/test substance in the spray mixture (g/l) | Active substances | BYF587 concentration (g/l) in the aqueous dilution | % penetration BYF587 after 7 h n = 5-7 | % penetration BYF587 after 26 h n = 5-7 |
| 19 | SC100 | N-(3'4'-dichloro-5-fluorobiphenyl-2-yl)-3-(difluoromethyl)-1-methyl-1H-pyrazole-4-carboxamide | 0.25 | 0.8 | 1.6 |
| 20 | EC200/N,N-Dimethyldecanamide** (0.5 g/l) | N-(3'4'-dichloro-5-fluorobiphenyl-2-yl)-3-(difluoromethyl)-1-methyl-1H-pyrazole-4-carboxamide | 0.25 | 25.7 | 40.7 |
| 21 | EC200/N,N-Dimethyldecanamide** (1.5 g/l) | N-(3'4'-dichloro-5-fluorobiphenyl-2-yl)-3-(difluoromethyl)-1-methyl-1H-pyrazole-4-carboxamide | 0.25 | 38.9 | 54.3 |

(*1)boiling point: 220-290° C.
**Hallcomid M8-10
***commercial tank mix additive with ethyl/methyl oleate as main constituent
****commercial tank mix additive, mineral oil concentrate

The invention claimed is:

1. A method for promoting the penetration of one or more agrochemical active substances into plants, comprising, applying to said plants one or more carboxamides of the formula (I)

$$R^1-CO-NR^2R^3 \quad (I)$$

in which
$R^1$ represents an unbranched, saturated alkyl group having 5 to 11 carbon atoms,
$R^2$ represents $C_1$-$C_6$-alkyl, and
$R^3$ represents H or $C_1$-$C_6$-alkyl, wherein said one or more agrochemical active substances is a mixture of prothioconazole with tebuconazole.

2. The method according to claim 1 wherein the one or more carboxamides of formula (I) is N,N-dimethyl n-octanamide or N,N-dimethyl n-decanamide.

3. The method according to claim 2 wherein the one or more carboxamides of formula (I) is N,N-dimethyl n-decanamide.

4. A method for promoting the penetration of one or more agrochemical active substances into plants, comprising, applying to said plants one or more carboxamides of the formula (I)

$$R^1-CO-NR^2R^3 \quad (I)$$

in which
$R^1$ represents an unbranched, saturated alkyl group having 5 to 11 carbon atoms,
$R^2$ represents $C_1$-$C_6$-alkyl, and
$R^3$ represents H or $C_1$-$C_6$-alkyl, wherein said one or more agrochemical active substances is a mixture of prothioconazole with spiroxamine.

5. The method according to claim 4 wherein the one or more carboxamides of formula (I) is N,N-dimethyl n-octanamide or N,N-dimethyl n-decanamide.

6. The method according to claim 5 wherein the one or more carboxamides of formula (I) is N,N-dimethyl n-decanamide.

7. A plant protection composition comprising,
a) 1 to 80% of one or more carboxamides of the formula (I), $$R^1-CO-NR^2R^3 \quad (I)$$

wherein
$R^1$ represents an unbranched, saturated alkyl group having 5 to 11 carbon atoms,
$R^2$ represents $C_1$-$C_6$-alkyl, and
$R^3$ represents H or $C_1$-$C_6$-alkyl,
b) 1 to 90% of one or more agrochemical active substances, wherein said one or more agrochemical active substances is a mixture of prothioconazole with tebuconazole, and
c) 0 to 98% of additives wherein the percentages are percent by weight.

8. The plant protection composition according to claim 7 wherein the one or more carboxamides of the formula (I) is N,N-dimethyl n-octanamide or N,N-dimethyl n-decanamide.

9. The plant protection composition according to claim 8 wherein the one or more carboxamides of formula (I) is N,N-dimethyl n-decanamide.

10. A plant protection composition comprising,
a) 1 to 80% of one or more carboxamides of the formula (I), $$R^1-CO-NR^2R^3 \quad (I)$$

wherein
$R^1$ represents an unbranched, saturated alkyl group having 5 to 11 carbon atoms,
$R^2$ represents $C_1$-$C_6$-alkyl, and
$R^3$ represents H or $C_1$-$C_6$-alkyl,
b) 1 to 90% of one or more agrochemical active substances, wherein said one or more agrochemical active substances is a mixture of prothioconazole with spiroxamine, and
c) 0 to 98% of additives wherein the percentages are percent by weight.

11. The plant protection composition according to claim 10 wherein the one or more carboxamides of the formula (I) is N,N-dimethyl n-octanamide or N,N-dimethyl n-decanamide.

12. The plant protection composition according to claim 11 wherein the one or more carboxamides of formula (I) is N,N-dimethyl n-decanamide.

13. A method according to claim 1, wherein said one or more carboxamides are formulated into a plant protection composition comprising,
a) 1 to 90% of one or more agrochemical active substances,
b) 1 to 90% of one or more carboxamides of the formula (I), and
c) 0 to 98% of other additives, wherein the percentages are percent by weight, and wherein the one or more agrochemical active substances comprises a mixture of prothioconazole with tebuconazole.

14. The method according to claim 13 wherein the one or more carboxamides of formula (I) is N,N-dimethyl n-octanamide or N,N-dimethyl n-decanamide.

15. The method according to claim 14 wherein the one or more carboxamides of formula (I) is N,N-dimethyl n-decanamide.

16. A method according to claim 1, wherein said one or more carboxamides are formulated into a plant protection composition comprising, P a) 1 to 90% of one or more agrochemical active substances, b) 1 to 90% of one or more carboxamides of the formula (I), and c) 0 to 98% of other additives, wherein the percentages are percent by weight, and wherein the one or more agrochemical active substances comprises a mixture of prothioconazole with spiroxamine.

17. The method according to claim 16 wherein the one or more carboxamides of formula (I) is N,N-dimethyl n-octanamide or N,N-dimethyl n-decanamide.

18. The method according to claim 17 wherein the one or more carboxamides of formula (I) is N,N-dimethyl n-decanamide.

* * * * *